United States Patent

Negele et al.

Patent Number: 5,254,696
Date of Patent: Oct. 19, 1993

[54] N-ACYLPYRROLIDINE DERIVATIVES

[75] Inventors: Michael Negele, Cologne; Bernd Baasner, Bergisch-Gladbach; Heinz-Jürgen Bertram, Holzminden; Jürgen Hartwig, Leverkusen, all of Fed. Rep. of Germany

[73] Assignee: Bayer Aktiengesellschaft, Leverkusen, Fed. Rep. of Germany

[21] Appl. No.: 917,547

[22] Filed: Jul. 21, 1992

Related U.S. Application Data

[62] Division of Ser. No. 754,883, Sep. 4, 1991, Pat. No. 5,171,355.

Foreign Application Priority Data

Sep. 13, 1990 [DE] Fed. Rep. of Germany ....... 4029054

[51] Int. Cl.$^5$ .................. C07D 207/08; C07D 207/16
[52] U.S. Cl. ..................................... 548/531; 548/566; 548/570; 548/577; 548/579
[58] Field of Search ............... 548/531, 566, 570, 577, 548/579

[56] References Cited

U.S. PATENT DOCUMENTS

| | | | |
|---|---|---|---|
| 4,912,127 | 3/1990 | Henning et al. | 514/422 |
| 4,912,128 | 3/1990 | Henning et al. | 514/422 |
| 4,912,232 | 3/1990 | Mullins et al. | 548/539 |
| 5,036,153 | 7/1991 | Braish et al. | 548/542 |

FOREIGN PATENT DOCUMENTS 0201742 11/1986 European Pat. Off. .

OTHER PUBLICATIONS

Chemical Abstracts, vol. 52; No. 8; Apr. 25, 1958, 6175b-d, Zakharkin.
Organic Reactions, Modern Methods to Prepare Monofluoroaliphatic Compounds, C. M. Sharts & W. A. Sheppard, pp. 125, 130–131 (1974).
ACS Symposium Series, M. Joan Comstock (1990), pp. 1–7, (Chapter 1 by John T. Welsh).
Tetrahedron, vol. 34; p. 3; M. Schlosser (1978).
G. V. Shustov, "Fluorodeoxygenation of Proline, Optically Active 2-Trifluoromethylpyrrolidine, and Its Chromophoric Derivatives," Jul., 1988, pp. 1606–1612 (an English translation from Izvestiya Akademii Nauk SSSR, Seriya Khimicheskaya).

Primary Examiner—Patricia L. Morris
Attorney, Agent, or Firm—Sprung Horn Kramer & Woods

[57] ABSTRACT

Novel pyrrolidine derivatives of the formula

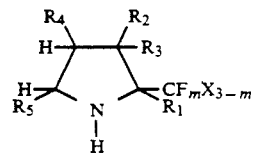

in which $R_1$, $R_2$, $R_3$, $R_4$ and $R_5$ have the meaning specified in the description,
X represents hydrogen, fluorine, chlorine, bromine or optionally substituted $C_1$-$C_4$-alkyl, and m represents 1, 2 or 3.

2 Claims, No Drawings

N-ACYLPYRROLIDINE DERIVATIVES

This is a division of application Ser. No. 07/754,883, filed Sep. 4, 1991 now U.S. Pat. No. 5,121,355.

The invention relates to novel N-acylpyrrolidine derivatives, to novel intermediates and processes for the preparation of the novel N-acylpyrrolidine derivatives, and to their use as herbicides and nematicides.

There were found novel N-acylpyrrolidine derivatives of the general formula

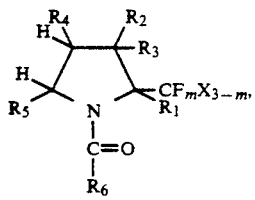

in which $R_1$, $R_2$ and $R_3$ independently of one another represent hydrogen, halogen, alkyl or aryl, $R_4$ represents hydrogen, halogen, cyano, alkyl, aryl or

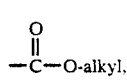

$R_5$ represents hydrogen, alkyl or aryl, $R_6$ represents alkyl or aryl,

X represents hydrogen, halogen or alkyl, and m represents 1, 2 or 3.

All alkyl radicals can be straight-chain or branched. Furthermore, all alkyl and aryl radicals can optionally be substituted.

Furthermore, it has been found that the novel N-acylpyrrolidine derivatives of the formula (I) derivatives of the formula (I)

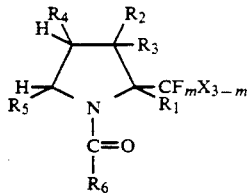

in which $R_1$, $R_2$, $R_3$, $R_4$, $R_5$, $R_6$, X and m have the abovementioned meaning are obtained when pyrrolidine derivatives of the formula

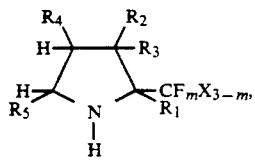

in which $R_1$, $R_2$, $R_3$, $R_4$, $R_5$, X and m have the abovementioned meaning are reacted with acid halides of the formula

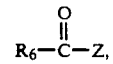

in which $R_6$ has the abovementioned meaning and z represents halogen, in particular bromine or chlorine, if appropriate in the presence of a diluent and if appropriate in the presence of an acid-binding agent.

Finally, it has been found that the novel N-acylpyrrolidine derivatives of the formula (I) have a good action as nematicides as well as for combating undesired plant growth.

Formula (I) provides a general definition of the novel N-acylpyrrolidine derivatives according to the invention. Preferred compounds of the formula (I) are those in which $R_1$, $R_2$ and $R_3$ independently of one another represent hydrogen, fluorine, chlorine, bromine, optionally substituted $C_1$-$C_6$-alkyl or optionally substituted $C_6$-$C_{10}$-aryl, $R_4$ represents hydrogen, fluorine, chlorine, bromine, cyano, optionally substituted $C_1$-$C_6$-alkyl, optionally substituted $C_6$-$C_{10}$-aryl or

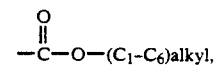

$R_5$ represents hydrogen, optionally substituted $C_1$-$C_6$-alkyl or optionally substituted $C_6$-$C_{10}$-aryl, $R_6$ represents optionally substituted $C_1$-$C_6$-alkyl or optionally substituted $C_6$-$C_{10}$-aryl, x represents hydrogen, fluorine, chlorine, bromine or optionally substituted $C_1$-$C_4$-alkyl, and m represents 1, 2 or 3, where the following are in each case suitable as alkyl substituents in the definitions of $R_1$, $R_2$, $R_3$, $R_4$, $R_5$, $R_6$ and X: fluorine, chlorine, bromine, hydroxyl, methoxy or ethoxy, and the following are in each case suitable as aryl substituents in the definitions of $R_1$, $R_2$, $R_3$, $R_4$, $R_5$ and $R_6$: fluorine, chlorine, bromine, $C_1$-$C_4$-alkyl or $C_1$-$C_4$-alkoxy.

Particularly preferred compounds of the formula (I) are those in which $R_1$ represents hydrogen, fluorine, chlorine, bromine, methyl, ethyl, n-propyl, i-propyl, n-butyl, s-butyl, i-butyl, t-butyl, phenyl or naphthyl, $R_2$ represents hydrogen, fluorine, chlorine, bromine, methyl, ethyl, phenyl or naphthyl, $R_3$ represents hydrogen, fluorine, chlorine, bromine, methyl or ethyl, $R_4$ represents hydrogen, fluorine, chlorine, bromine, cyano, methyl, ethyl, phenyl, methoxycarbonyl or ethoxycarbonyl, $R_5$ represents methyl, ethyl, n-propyl, i-propyl, n-butyl, i-butyl, s-butyl, t-butyl or phenyl, $R_6$ represents methyl, ethyl, n-propyl, i-propyl, n-butyl, i-butyl, s-butyl or t-butyl, or represents phenyl which is optionally monosubstituted to trisubstituted by identical or different substituents from the series comprising fluorine, chlorine, bromine, methyl, methoxy, hydroxyl, trifluoromethyl, trifluoromethoxy and trifluoromethylthio, X represents hydrogen, chlorine, bromine, methyl or ethyl, and m represents 1, 2 or 3.

Very particularly preferred compounds of the formula (I) are those in which

R₁ represents hydrogen, fluorine, chlorine or methyl,
R₂ represents hydrogen or methyl,
R₃ represents hydrogen,
R₄ represents hydrogen,
R₅ represents hydrogen, fluorine, chlorine or methyl,
R₆ represents methyl, ethyl, n-propyl, i-propyl, n-butyl, i-butyl, s-butyl or t-butyl, or represents phenyl which is optionally monosubstituted or disubstituted by identical or different substituents from the series comprising fluorine, chlorine and trifluoromethyl, and
m represents 3.

If, for example, 2-trifluoromethyl-2-methyl-pyrrolidine and 2,6-dichlorobenzoyl chloride are used as starting substances, the course of the reaction of the process according to the invention may be illustrated by the following equation:

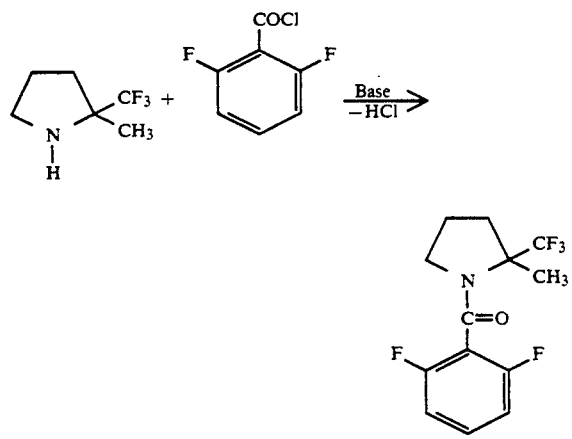

Formula (II) provides a general definition of the pyrrolidine derivatives to be used as starting substances in the process according to the invention for the preparation of compounds of the formula (I).

In formula (II), $R_1$, $R_2$, $R_3$, $R_4$, $R_5$, X and m preferably, or in particular, have those meanings which have already been mentioned above in connection with the description of the compounds of the formula (I) according to the invention as being preferred, or particularly preferred, for $R_1$, $R_2$, $R_3$, $R_4$, $R_5$, X and m.

The pyrrolidine derivatives of the formula (II) are novel and equally a subject of the present invention. The compound 2-trifluoromethylpyrrolidine is excluded (cf. Isv. Akad. Nauk SSSR, Ser. Khim., 1422 (1988)).

The novel pyrrolidine derivatives of the formula (II) are obtained by a process in which a) nitroalkyl compounds of the formula (IV)

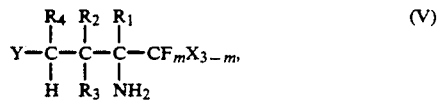

in which
$R_1$, $R_2$, $R_3$, $R_4$, X and m have the abovementioned meaning and
y represents —COR₅ or —CN, where
R₅ has the abovementioned meaning, are reduced intermediately to give the corresponding aminoalkyl compounds of the formula $$Y-\underset{H}{\overset{R_4}{C}}-\underset{R_3}{\overset{R_2}{C}}-\underset{NH_2}{\overset{R_1}{C}}-CF_mX_{3-m}, \quad (V)$$

in which
$R_1$, $R_2$, $R_3$, $R_4$ r X, m and Y have the abovementioned meaning, and the compounds of the formula (V) are cyclised at temperatures between 25° and 150° C., preferably between 40° and 900° C., preferably without intermediate isolation, and if appropriate in the presence of a diluent such as, for example, methanol or ethanol. Examples of reducing agents which can be used are all customary reducing agents such as, for example, complex alkali metal hydrides such as lithium aluminium hydride.

It is preferred to use hydrogen under a partial pressure of 5 to 150 bar, preferably 40 to 80 bar, in the presence of suitable catalysts such as, for example, Raney nickel, palladium/active carbon or copper chromite.

The product can be worked up, for example, by filtration, extraction of the pyrrolidine derivative, for example using ether, and subsequent distillation.

Alternatively, the pyrrolidine derivative of the formula (II) can also be precipitated in hydrochloride form by adding aqueous hydrochloric acid after the filtration. The pyrrolidine derivative (II) can then again be set free from the hydrochloride by treatment with aqueous alkali metal hydroxide solution, and can be isolated by extraction, for example using diethyl ether, and subsequent distillation.

The pyrrolidine derivatives of the formula (II) are obtained as racemates/diastereomer mixtures. A resolution or concentration can be effected by known processes. (cf. DE-OS (German Offenlegungsschrift) 3,739,784).

Alternatively, the novel pyrrolidine derivatives of the formula (II) can be obtained when b) pyrrolidinone derivatives of the formula (VI)

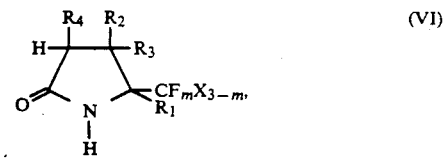

in which
$R_1$, $R_2$, $R_3$, $R_4$, X and m have the abovementioned meaning, are hydrogenated under drastic conditions, for example with hydrogen at a pressure of 150–250 bar, preferably at 180–200 bar, in the presence of a suitable catalyst such as, for example, Raney nickel or copper chromite, at temperatures between 150° and 280° C., preferably 186° and 120° C., if appropriate in the presence of a diluent, such as, for example, methanol or water.

Formula (VI) provides a general definition of the pyrrolidinone derivatives.

In Formula (VI), $R_1$, $R_2$, $R_3$, $R_4$, X and m preferably, or in particular, have those meanings which have already been mentioned above in connection with the description of the compounds of the formula (I) according to the invention as being preferred, or particularly preferred, for $R_1$, $R_2$, $R_3$, $R_4$, X and m.

The pyrrolidinone derivatives of the formula (VI) are also novel and a subject of the present invention.

The novel pyrrolidinone derivatives of the formula (VI) can be prepared by a process in which nitroalkyl compounds of the formula (VII)

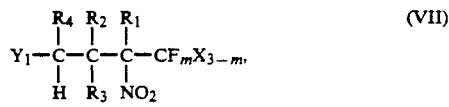

in which $R_1$, $R_2$, $R_3$, $R_4$, X and m have the abovementioned meaning and $Y_1$ represents —COOR$_7$ where $R_7$ represents hydrogen or $C_1$-$C_6$-alkyl, are reduced intermediately to give the corresponding aminoalkyl compounds of the formula (VIII)

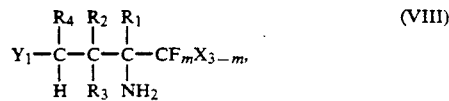

in which $R_1$, $R_2$, $R_3$, $R_4$, X, m and $Y_1$ have the abovementioned meaning, and the compounds of the formula (VIII) are cyclised at temperatures between 25° and 130° C., preferably 50° and 90° C., preferably without intermediate isolation, if appropriate in the presence of a diluent such as, for example, alcohols, such as methanol, or ethers, such as diethyl ether, tetrahydrofuran or dioxane, or water.

Examples of suitable reducing agents are complex alkali metal hydrides such as lithium aluminium hydride or hydrogen at a pressure of 5-150 bar, preferably 60-90 bar, in the presence of suitable catalysts such as noble metal catalysts of sub-group VIII on support materials such as, for example, barium sulphate, aluminium oxide or carbon, furthermore Raney nickel, Raney cobalt. Palladium/active carbon is preferably used.

The mixture can be worked up, for example, by filtration, removal of the diluent and distillation or recrystallisation.

The pyrrolidinone derivatives of the formula (VI) are obtained in the form of racemates/diastereomer mixtures. They can be resolved or concentrated by known processes (cf., for example, DE-OS (German Offenlegungsschrift) 3,739,784).

The nitroalkyl compounds of the formulae (IV) and (VIII) are known and/or can be prepared analogously to known processes (cf., for example, DE-OS (German Offenlegungsschrift) 3,739,784; DE-OS (German Offenlegungsschrift) 3,808,276).

Formula (III) provides a general definition of the acid halides furthermore to be used as starting substances in the process according to the invention for the preparation of compounds of the formula (I).

In formula (III), $R_6$ preferably, or in particular, has that meaning which has already been mentioned above in connection with the description of the compounds of the formula (I) according to the invention as being preferred, or particularly preferred, for $R_6$. Z represents halogen, in particular chlorine or bromine.

Acid halides of the formula (III) are generally known compounds of organic chemistry.

Suitable diluents for carrying out the process according to the invention are, preferably, all inert organic solvents. These include, in particular, aliphatic and aromatic, optionally chlorinated hydrocarbons such as benzine, benzene, toluene, xylene, methylene chloride, chloroform, carbon tetrachloride, chlorobenzene and o-dichlorobenzene, ethers such as diethyl ether, diisopropyl ether, dioxane and tetrahydrofuran, ketones such as acetone, butanone, methyl isopropyl ketone and methyl isobutyl ketone, nitriles such as acetonitrile and propionitrile, and the highly-polar solvents dimethylsulphoxide and hexamethylphosphoric triamide.

The process according to the invention is preferably carried out in the presence of a suitable acid-binding agent. Suitable acid-binding agents are all inorganic and organic bases which can customarily be used. The following are preferably used: alkali metal alcoholates such as sodium tert-butylate or potassium tert-butylate, sodium tert-amylate or potassium tert-amylate, alkali metal carbonates such as, for example, sodium carbonate, potassium carbonate and sodium hydrogen carbonate, furthermore lower tertiary alkylamines, cycloalkylamines or arylalkylamines such as, for example, triethylamine, N,N-dimethyl-benzylamine, furthermore pyridine, and also 1,4-diazabicyclo[2.2.2]octane and 1,5-diazabicyclo[4.3.0]non-5-ene.

When carrying out the process according to the invention, the reaction temperatures can be varied within a substantial range. In general, the process is carried out at temperatures between −30° C. and +200° C., preferably a temperatures between 0° C. and +110° C.

In general, the process according to the invention is carried out under atmospheric pressure. For carrying out the process according to the invention, the starting substances to be used are generally employed in approximately equimolar amounts. However, an excess of one or the other component up to about 10% causes no problems.

When carrying out the process according to the invention, the reaction is preferably carried out using one of the abovementioned acid-binding agents in one of the above-mentioned diluents. The reaction mixture is stirred for one hour at the temperature required. The reaction mixture is worked up and the reaction products of the formula (I) according to the invention are isolated in a generally customary fashion.

The active compounds of the formula (I) according to the invention have a powerful action against nematodes and can furthermore be employed in practice for combating undesired plant growth. The active substances are suitable for use as plant protection agents, in particular as herbicides and nematicides.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants.

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention are furthermore outstandingly suitable for combating animal pests, preferably nematodes.

The phytoparasitic nematodes include Pratylenchus spp., *Radopholus similis, Ditylenchus dipsaci, Tylenchulus semipenetrans,* Heterodera Spp., Meloidogyne Spp., Aphelenchoides spp., Longidorus spp., Xiphinema spp., Trichodorus spp., *Globodera rostochiensis.*

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, or such as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

For combating weeds, the active compounds according to the invention, as such or in the form of their formulations, can also be used as mixtures with known herbicides, finished formulations or tank mixes being possible.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

PREPARATION EXAMPLES

Example 1

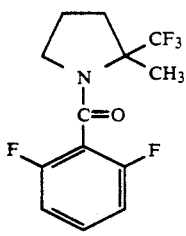

A solution of 8.83 g (0.05 mol) of 2,6-difluorobenzoyl chloride in 10 ml of tetrahydrofuran (THF), to which 5.6 g (0.055 mol) of triethylamine had been added, was added dropwise to a solution of 7.65 g (0.05 mol) of 2-trifluoromethyl-2-methylpyrrolidine in 25 ml of tetrahydrofuran (THF). The reaction is exothermic, and slow dropwise addition prevented the temperature from rising above +35° C. Stirring was continued for one hour at room temperature, and the mixture was then poured into 250 ml of ice-water and acidified using dilute hydrochloric acid, and the precipitate obtained was filtered off with suction, washed thoroughly with water and dried. 9.96 g (68% yield of theory) of N-(2,6-difluorobenzoyl)-2-trifluoromethyl-2-methyl-pyrrolidine of melting point 119°–120° C. are obtained.

Example 2

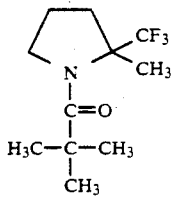

A solution of 6.03 g (0.05 mol) of 2,2-dimethylpropionyl chloride in 25 ml of THF was added dropwise to a solution of 7.65 g (0.05 mol) of 2-trifluoromethyl-2-methylpyrrolidine in 15 ml of THF, to which 5.6 g (0.055 mol) of triethylamine had been added. The course of the reaction is exothermic. The dropwise addition was effected slowly enough that the temperature did not rise to above 35° C. Stirring was continued for one hour at room temperature, and the mixture was then poured into 200 ml of ice-water, the pH was adjusted to 4–5 using dilute hydrochloric acid, and the mixture was extracted twice using 60 ml portions of dichloromethane. The combined organic phases were dried over magnesium sulphate and filtered, and the solvent was stripped off under a water pump vacuum. The oil which remained was chromatographed over a short silica gel column (mobile phase toluene/ethyl acetate 1:1). After the mobile phase had been removed, 9.12 g (77% yield of theory) of N-pivaloyl-2-trifluoromethyl-2-methylpyrrolidine are obtained as a pale yellow oil having a refractive index of $n_D^{20}$: 1,4615 (GC purity: 97.7%).

Example 3

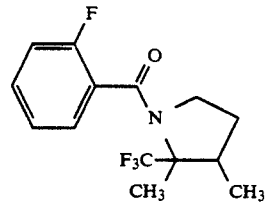

1.6 g (0.01 mol) of 2-fluorobenzoyl chloride were dissolved in 100 ml of absolute tetrahydrofuran. A solution of 1.4 ml (0.01 mol) of triethylamine and 1.67 g (0.01 mol) of 2,3-dimethyl-2-trifluoromethyl-pyrrolidine, dissolved in 10 ml of absolute tetrahydrofuran, was slowly added dropwise at 0° C. When the addition had ended, the batch was allowed to come to room temperature, and stirring was continued for one hour. For working up, 50 ml of methylene chloride were added, and the mixture was then washed in succession with 2 N hydrochloric acid, saturated NAHCO₃ solution and saturated NaCl solution. To purify the crude product, the mixture was chromatographed (mobile phase mixture: ethyl acetate/cyclohexane 1:2).

2.5 g (86%) of N-(2-fluorobenzoyl)-2,3-dimethyl-2-trifluoromethyl-pyrrolidine with the data:
$^1$H-NMR(CDCl₃, 200 MHz) : 1.115 d, J=70Hz (3H); 1.35–1.95 m (2H); 2.60 m (1H); 1.70 s (3H); 3.35 m (2H); 7.04–7.38 m (4H) are obtained.

The compounds of the general formula (I) which are listed in Table 1 can be prepared analogously to the Preparation Examples and following the general instructions for the process according to the invention $$\text{(I)}$$

(structure of formula I with substituents R₁, R₂, R₃, R₄, R₅, R₆, H, N, C=O, CF$_m$X$_{3-m}$)

TABLE 1

| Example No. | R₁ | R₂ | R₃ | R₄ | R₅ | R₆ | —CF$_m$X$_{3-m}$ | Physical Data |
|---|---|---|---|---|---|---|---|---|
| 4 | CH₃ | CH₃ | H | H | H | 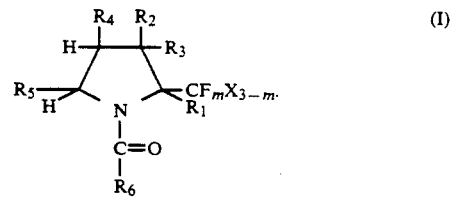 | CF₃ | M.p. 66–67° C. |

TABLE 1-continued

| Example No. | $R_1$ | $R_2$ | $R_3$ | $R_4$ | $R_5$ | $R_6$ | $-CF_mX_{3-m}$ | Physical Data |
|---|---|---|---|---|---|---|---|---|
| 5 | $CH_3$ | H | H | H | $CH_3$ | 2-fluorophenyl | $CF_3$ | M.p. 94–96° C. |
| 6 | $CH_3$ | H | H | H | $CH_3$ | 2,3-difluorophenyl | $CF_3$ | M.p. 103–104° C. |
| 7 | $CH_3$ | H | H | H | H | 2-fluorophenyl | $CF_3$ | Oil, IR: 2980; 1660; 1455 cm$^{-1}$ |
| 8 | H | H | H | H | $CH_3$ | 2-fluorophenyl | $CF_3$ | Oil, IR: 2950; 1655; 1380 cm$^{-1}$ |
| 9 | H | H | H | H | $CH_3$ | 4-chlorophenyl | $CF_3$ | M.p. 72–74° C. |
| 10 | H | H | H | H | H | 2-fluorophenyl | $CF_3$ | Oil, IR: 2950; 1660; 1390 cm$^{-1}$ |
| 11 | $CH_3$ | H | H | H | H | 3,4-dichlorophenyl | $CF_3$ | M.p. 92–93° C. |
| 12 | $CH_3$ | H | H | H | $CH_3$ | 3,4-dichlorophenyl | $CF_3$ | M.P. 92–94° C. |
| 13 | $CH_3$ | $CH_3$ | H | H | H | 3,4-dichlorophenyl | $CF_3$ | M.p. 58–60° C. |
| 14 | H | H | H | H | $CH_3$ | 4-(trifluoromethyl)phenyl | $CF_3$ | Oil, IR: 2970; 1660; 1385 cm$^{-1}$ |

PREPARATION OF THE STARTING COMPOUNDS a) of the formula (II)

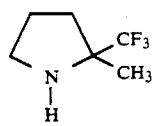

Variant A

In a V4A stirred autoclave of volume 0.7 l, 100 g (0.5 mol) of 4-(trifluoromethyl)-4-nitropentan-1-al were hydrogenated at 80° C. for 8 hours in 300 ml of methanol on 10 g of Raney nickel. The hydrogen partial pressure was 80 bar; 90% of the theoretic amount of hydrogen was taken up. For working up, the catalyst was filtered off and rinsed with a little methanol. The methanolic solution was rendered acidic using 100 ml of concentrated hydrochloric acid and concentrated to dryness under reduced pressure. The results were 59 g (0.34 mol) of 2-trifluoromethyl-2-methyl-pyrrolidine hydrochloride (67% of theory). 2-Trifluoromethyl-2-methyl-pyrrolidine (b.p.$_{1013}$: 115°–118° C.) was obtained from the hydrochloride by adding an equimolar amount of sodium hydroxide solution, extraction with diethyl ether, drying over sodium sulphate followed by removal of the solvent by distillation over a Vigreux column of 30 cm in length.

Example 16

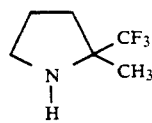

Variant B

In a V4A stirred autoclave of volume 0.7 l, 98 g (0.5 mol) of 4-(trifluoromethyl)-4-nitropentanecarbonitrile were hydrogenated for 8 hours at 100° C. in 300 ml of methanol on 10 g of Raney nickel. The hydrogen partial pressure was 70–80 bar, 85% of the theoretic amount of hydrogen was taken up. For working up, the catalyst was filtered off and washed with a little methanol. The further procedure was as in Example 15. 57 g (0.3 mol) of 2-trifluoromethyl-2-methyl-pyrrolidine hydrochloride were obtained (60% of theory).

Example 17

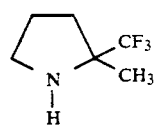

Variant C

In a 0.3 l V4A stirred autoclave, 41.5 g (0.25 mol) of 5-trifluoromethyl-5-methyl-pyrrolidin-2-one were hydrogenated for 16 hours at 180°–190° C. in 100 ml of methanol on 5 g of copper chromite (CuCr$_2$O$_4$). The hydrogen partial pressure was 220–240 bar; 80% of the theoretic amount of hydrogen was taken up. Working-up was analogous to Example 15.

25 g (0.13 mol) of 2-trifluoromethyl-2-methyl-pyrrolidine hydrochloride were obtained (53% of theory).

The compounds of the general formula (II) listed in Table 2 can be prepared analogously to Examples 15, 16 and 17 and following the general instructions

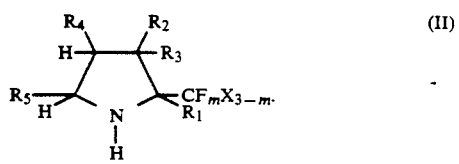

TABLE 2

| Example No. | Variant | R$_1$ | R$_2$ | R$_3$ | R$_4$ | R$_5$ | —CF$_M$X$_{3-m}$ | Physical Data |
|---|---|---|---|---|---|---|---|---|
| 18 | A | H | H | H | H | CH$_3$ | CF$_3$ | B.p.$_{1013}$: 118–120° C. |
| 19 | A | CH$_3$ | H | H | H | CH$_3$ | CF$_3$ | B.p.$_{1013}$: 125–126° C. |
| 20 | A | CH$_3$ | CH$_3$ | H | H | H | CF$_3$ | B.p.$_{1013}$: 121–124° C. |
| 21 | A,C | H | H | H | H | H | CF$_3$ | *) |

*) see Isv. Akad. Nauk SSSR, Ser. Khim, 1422 (1988)

b) of the formula (VI)

Example 22

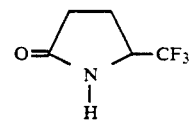

In a V4A stirred autoclave of volume 0.7 l, 108 g (0.50 mol) of methyl 5,5,5-trifluoro-4-nitropentanecarboxylate were hydrogenated at 60° C. for 6 hours in 300 ml of methanol on 10 g of 5% palladium-on-carbon. The hydrogen partial pressure was 60 bar, 95% of the theoretic amount of hydrogen were taken up. For working up, the catalyst was filtered off and rinsed with a little methanol. The solvent was removed by distillation under a water pump vacuum, first at 40° C. and then at 80° C. During this process, the residue began to solidify. For further purification, a distillation under water pump vacuum was carried out.

57 g (0.37 mol) of 5-trifluoromethyl-pyrrolidin-2-one of boiling point b.p.$_{14}$: 122°–124° C. were obtained (74.5% of theory).

Example 23

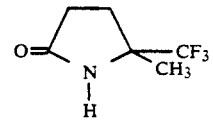

115 g (0.5 mol) of methyl 4-trifluoromethyl-4-nitropentanecarboxylate were reacted and worked up analogously to Example 22.

After recrystallisation from ligroin, 72 g (0.43 mol) of 5-trifluoromethyl-5-methyl-pyrrolidin-2-one of melting point 111°-112° C. were obtained (86% of theory).

USE EXAMPLES

Example A-1

One part by weight of the compound obtained in Example 9 was mixed with 4 parts by weight of acetone, 1 part by weight of alkylaryl polyglycol ether was added as the emulsifier, and the mixture was diluted with water. In this way, a preparation of an active compound was obtained.

This preparation was intimately mixed with soil which was heavily infested with *Globodera rostochiensis* (=test nematodes). The concentration of the active compound in the preparation is of virtually no importance, only the amount of the active compound per unit volume of soil is decisive. This amount was 20 ppm (=mg/l). The soil which has been treated in this way was filled into pots, potatoes were planted, and the pots were kept in a greenhouse at 20° C.

After 6 weeks, the potato roots were examined for cysts. It was found that the preparation of the active compound had suppressed 95% of the infestation in a comparison with controlled plants in soil which was untreated, but infested in the same manner.

Example A-2

One part by weight of the compound obtained in Example 14 was mixed with 4 parts by weight of acetone, 1 part by weight of alkylaryl polyglycol ether was added as the emulsifier, and the mixture was diluted with water. In this way, a preparation of an active compound was obtained.

This preparation was intimately mixed with soil which was heavily infested with Meloidogyne incognita (=test nematodes). The concentration of the active compound in the preparation is of virtually no importance, only the amount of the active compound per unit volume of soil is decisive. This amount was 20 ppm (=mg/l). The soil which has been treated in this way was filled into pots, lettuce was sown, and the pots were kept in a greenhouse at 250° C.

After 4 weeks, the salad roots were examined for cysts. It was found that the preparation of the active compound had suppressed 95% of the infestation in a comparison with controlled plants in soil which was untreated, but infested in the same manner.

What is claimed is:

1. A pyrrolidine derivative of the formula

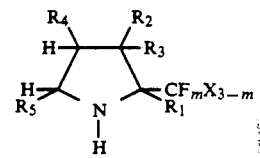

in which $R_1$, $R_2$ and $R_3$ independently of one another represent hydrogen, fluorine, chlorine, bromine, optionally substituted $C_1-C_5$-alkyl or optionally substituted $C_5-C_{10}$-aryl, $R_4$ represents hydrogen, fluorine, chlorine, bromine, cyano, optionally substituted $C_1-C_5$-alkyl, optionally substituted $C_5-C_{10}$-aryl or

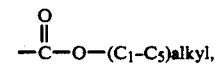

$R_5$ represents hydrogen, optionally substituted $C_1-C_5$-alkyl or optionally substituted $C_6-C_{10}$-aryl, X represents hydrogen, fluorine, chlorine, bromine or optionally substituted $C_1-C_4$-alkyl, and m represents 1, 2 or 3, the optional substituents on alkyl in the definitions of $R_1$, $R_2$, $R_3$, $R_4$, $R_5$ and X being selected from the group consisting of fluorine, chlorine, bromine, hydroxyl, methoxy and ethoxy, and the optional substituents on aryl in the definitions of $R_1$, $R_2$, $R_3$, $R_4$, $R_5$ being selected from the group consisting of fluorine, chlorine, bromine, $C_1-C_4$-alkyl and $C_1-C_4$-alkoxy, with the exception of the compound 2-trifluoromethyl-pyrrolidine.

2. A pyrrolidine derivative according to claim 1, in which $R_1$ represents hydrogen, fluorine, chlorine, bromine, methyl, ethyl, n-propyl, i-propyl, n-butyl, s-butyl, i-butyl, t-butyl, phenyl or naphthyl, $R_2$ represents hydrogen, fluorine, chlorine, bromine, methyl, ethyl, phenyl or naphthyl, $R_3$ represents hydrogen, fluorine, chlorine, bromine, methyl or ethyl, $R_4$ represents hydrogen, fluorine, chlorine, bromine, cyano, methyl, ethyl, phenyl, methoxycarbonyl or ethoxycarbonyl, $R_5$ represents methyl, ethyl, n-propyl, i-propyl, n-butyl, i-butyl, s-butyl, t-butyl or phenyl, X represents hydrogen, chlorine, bromine, methyl or ethyl, and m represents 1, 2, or 3.

* * * * *